United States Patent
Danielson et al.

(10) Patent No.: US 6,436,089 B1
(45) Date of Patent: Aug. 20, 2002

(54) CONNECTING DEVICE FOR MEDICAL PURPOSES

(75) Inventors: Bo G. Danielson, Uppsala; Dick Persson, Los, both of (SE)

(73) Assignee: Hemapure AB, Uppsala (SE)

( * ) Notice: Subject to any disclaimer, the term of this patent is extended or adjusted under 35 U.S.C. 154(b) by 0 days.

(21) Appl. No.: 09/509,833

(22) PCT Filed: Oct. 20, 1998

(86) PCT No.: PCT/SE98/01880

§ 371 (c)(1),
(2), (4) Date: Jun. 5, 2000

(87) PCT Pub. No.: WO99/20338

PCT Pub. Date: Apr. 29, 1999

(30) Foreign Application Priority Data

Oct. 21, 1997 (SE) .............................................. 9703839

(51) Int. Cl.$^7$ ............................................. A61M 25/00
(52) U.S. Cl. ....................................... 604/523; 210/232
(58) Field of Search ........................ 604/288.03, 523, 604/4, 8, 175, 513; 138/89; 210/232, 641

(56) References Cited

U.S. PATENT DOCUMENTS

| | | | | |
|---|---|---|---|---|
| 4,108,173 A | | 8/1978 | Slivenko et al. .............. 128/214 |
| 4,164,221 A | * | 8/1979 | Bentley et al. .............. 604/513 |
| 4,708,802 A | * | 11/1987 | Rath et al. .................. 210/641 |
| 4,804,369 A | * | 2/1989 | Lapeyre et al. .............. 604/175 |
| 4,822,341 A | * | 4/1989 | Colone ........................ 604/175 |
| 4,898,669 A | * | 2/1990 | Tesio ........................... 210/232 |
| 4,983,162 A | | 1/1991 | Metais et al. ................... 604/43 |
| 5,147,321 A | * | 9/1992 | Slonina et al. .............. 604/175 |
| 5,374,239 A | * | 12/1994 | Mischenko .................... 604/8 |
| 5,474,526 A | * | 12/1995 | Danielson et al. ............. 604/4 |
| 5,931,801 A | * | 8/1999 | Burbank et al. ............... 604/4 |
| 5,983,947 A | * | 11/1999 | Utterberg ..................... 138/89 |
| 6,007,516 A | * | 12/1999 | Burbank et al. ....... 604/288.03 |

FOREIGN PATENT DOCUMENTS

WO      WO92/13590       8/1992

* cited by examiner

*Primary Examiner*—Teresa Walberg
*Assistant Examiner*—Leonid Fastovsky
(74) *Attorney, Agent, or Firm*—Jacobson Holman, PLLC

(57) ABSTRACT

Device for external connection of the bloodstream of a patient to an external circuit or a fluid source for medical purposes. The device includes a main body with at least a first opening being surrounded by first sealing surface (-s) and being adapted to be protected by a removable protective member. A connecting member with at least one second opening being arranged to be protected by a protective body which is removable with respect to the connecting member. The connecting member is connectable to the main body under simultaneous removal of the protective member and the protective body in order to obtain leakproof connection between the openings. The main body is provided with holding elements forming a guide which is open in both ends for the protective member and the connecting member respectively. The invention also concerns a connecting unit for the connecting device.

18 Claims, 7 Drawing Sheets

CONNECTING DEVICE FOR MEDICAL PURPOSES

FIELD OF THE INVENTION

This invention concerns a connecting device for medical purposes and a protective unit for use in such a device.

BACKGROUND OF THE INVENTION

WO 92/13590 (corresponds to SE-B-467 769) concerns such a device, wherein a housing is provided with inward sealing surfaces surrounding connecting openings which are adapted to co-operate with outward sealing surfaces surrounding conduit openings on a coupling member which communicates with an external circuit. The sealing surfaces of the housing as well as of the connecting member are covered and protected by protective members in a non-connected position which in the process of connecting are adapted to be removed from and thereby uncover the respective sealing surfaces for achieving a leakproof connection.

The purpose of protecting the sealing surfaces is to avoid contamination of these as well as of the channels and thereby avoid or at least radically reduce the infection risks encountered by a patient using the connecting device.

The device being known from the cited document functions well but is relatively complex, which has resulted in likewise complicated and thereby relatively expensive production.

SUMMARY OF THE INVENTION

It is an aim of this invention to set the said problems aside and to provide a development of the known device which with retained high hygienic standard is uncomplicated to produce, simple to handle and possible to produce at a reduced cost.

These aims are achieved in a device as above by the feature of the characterising portion of claim 1.

By the holding elements forming a guide which is open at both ends for parts to be connected (the protective member and the connecting member respectively) it is achieved that the connecting procedure may be accomplished by displacements of the part intended to be connected along said guide in one single displacement movement, whereby with this simple movement, as an example in case of connecting the connecting member, at the same time the protective member is removed from the main body and thereby its active position. The displacement of the connecting member to the connecting position thus results in that co-operation is obtained between the respective sealing surfaces at the same time as the protective body is brought from the position where it protects the second sealing surface (surfaces). It should be noted that a relative movement between the parts is intended and that in practice the protective body may be fixed while the other parts are subject to a movement. When disconnecting the connecting member after completed treatment, the invention provides a corresponding simultaneous placement of the protective member.

The connecting member thus does not have to be brought down into a housing in order to obtain the connecting position, which otherwise is the case with the prior art, where the housing is provided with inward sealing surfaces. This results in considerable simplified manufacture compared to the known device, since the respective sealing surfaces are located on a surface which extends along the guide, resulting in essentially simplified production. A further advantage is that the hygienic standard is further improved, since, according to the invention, no protective lid or the like has to be removed from the main body before the connecting procedure, which thus eliminates the need of exposing the inside of the housing before it is possible to connect the connecting member. Instead connection may be made with a totally "closed" main body. The main body hereby has no movable parts, which results in simplified and more economic manufacture and further better security and higher hygienic standard, in particular when it is applied as an implant.

By the sealing surfaces being plane, manufacture is simplified and the resulting product more economic.

One feature of the invention concerns the use of the device according to the invention as a so called blood vessel valve which is useful for medical purposes where access to the blood stream is desirable, for example when taking samples from the blood stream, administration of different medicals, nutrition, cell treatment, determining of levels of substances in the blood stream etc. The means for supporting growth may be flange-like, longitudinally oriented elements or the like. An implanted main body will have the skin level somewhat above these means and with the upper part with the guide etc. above the skin level and being accessible for connecting the respective elements. The construction according to the invention with an open guide configuration in this connection results in simplified handling for the patient and/or the medical personnel.

In use of the blood vessel valve for CRRT (Chronic Renal Replacement Therapy), blood treatment/dialysis and in a number of different applications i.e. connecting other types of artificial organs than artificial kidneys, in gas exchange such as oxidization etc. there are two coupling means and two first and two second openings in the device according to the invention. The construction of the main body hereby allows effective drawing of channels such as to effectively reduce the flow resistance in the device as a whole. All taken together, the device according to the invention is particularly preferred as a blood vessel valve.

Another feature according to the present invention results in that the coupling means are connected to each other in a simple way when the protective member is placed in its active position which in case of an implant assures that all the time there is a flow through the device, thus eliminating the formation of coagulated blood.

An aspect of the invention which considerably simplifies handling the device is where the protective body thus comprises a guiding means for simplified application, and when lockable and openable fastening means are present for co-operation with the main body, the user thus only needs to activate these means in order to obtain adequate guidance of the connecting member (or any other part), which means that the device will be essentially more simple to handle for the patient himself or the medical personnel in case of an implanted main body.

Another feature according to to the present invention allows direct access to the blood stream through a membrane which is penetratable with an injection needle.

The invention also concerns a connecting unit and a protective unit respectively for the use with a device.

BRIEF DESCRIPTION OF THE DRAWING

The invention will now be described in more detail with reference to the annexed drawings wherein.

DETAILED DESCRIPTION OF THE PREFERRED EMBODIMENTS

Figure 1A:
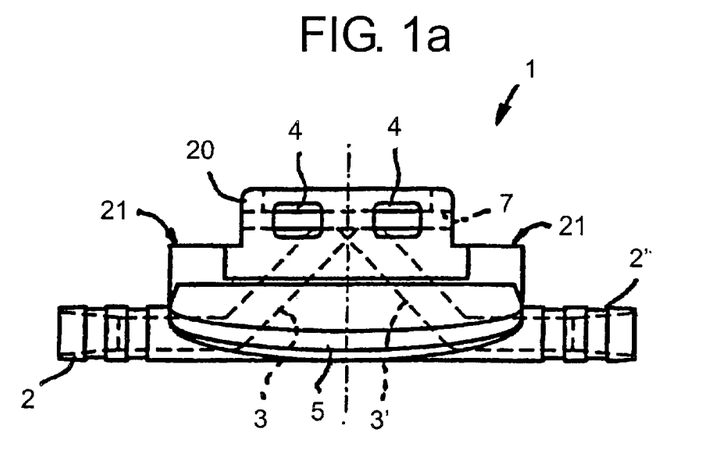
FIGS. 1a–1c show a main body in a side view, an end view and a plane view from above, respectively.
Figure 1B:
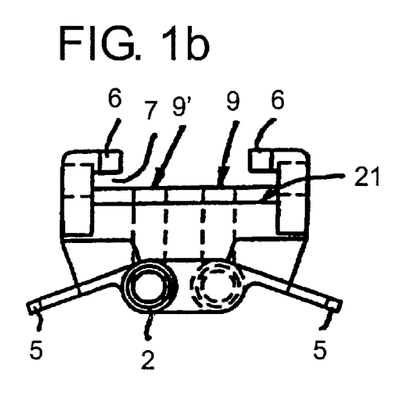
Figure 1C:
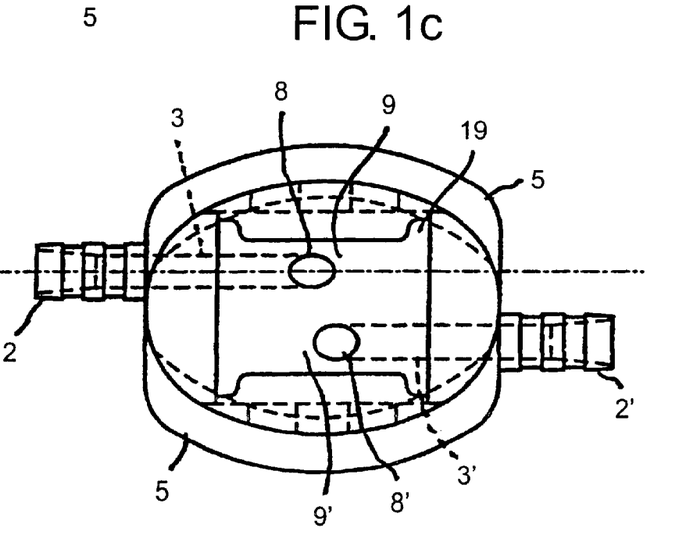

In FIG. 1a 1 indicates a main body having oppositely directed outgoing coupling means 2 and 2', which over channels 3 and 3' respectively are connected to first openings 8 and 8' respectively which are placed in a plane extending in parallel with the longitudinal direction of the main body, which is more evident on FIG. 1b and 1c. In the areas around the first openings 8, 8' portions of said plane comprises first sealing surfaces 9 and 9' respectively. In FIG. 1b further are shown holding elements 6 on the main body 1 which are L-shaped, longitudinal, inwardly directed rims which together with the plane providing the sealing surfaces 9, 9' forms a linear guide 7 (FIG. 1b) for co-operation with elements being intended to be connected to the main body. 4 indicates coupling openings allowing access to the guide 7 from the side in a way that will be further explained below. When the main body according to the invention is intended to be implanted, it is preferred that means 5 for supporting growth of human tissue are arranged which means in this case are outwardly directed flange-like wings with possible holes penetrating the material. C.f. FIG. 6c, wherein in growth holes/sewing holes 45' are made in the flange-like means 45.

From FIG. 1a it is further clear that the main body is made with an overstructure 20 for connecting purposes with respect to a basic plane 21, which in turn is located below the plane including the first sealing surfaces 9, 9'.

Figure 2A:
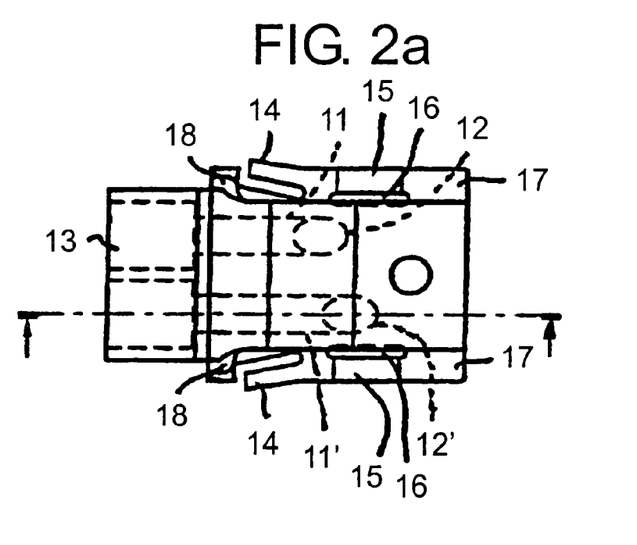
FIGS. 2a–2c show a connecting member in a plane view from above, a longitudinal section and an end view as seen in the direction against the insertion direction, respectively.

FIG. 2a shows a connecting member 10, which comprises conduits 11, 11' (indicated with interrupted lines) for the connection with an external circuit over a nipple portion 13 for the connection of tubing or the like. The connecting member 10 is further provided with holding means 17 formed as sideways directed linear flanges which are intended to co-operate with the holding elements 6 of the main body (see particularly FIG. 1b). Further 14 indicates sideways directed snap wings for locking co-operation with the openings 4 in the main body (see FIG. 1a). 18 indicates locking shoulders which prevent a connecting member 10 from being brought through the guide 7 of the main body, and these shoulders are intended to co-operate with shoulder recesses 19 in the main body (see FIG. 1c) for adequate positioning of the connecting member on the main body.

Figure 3A:
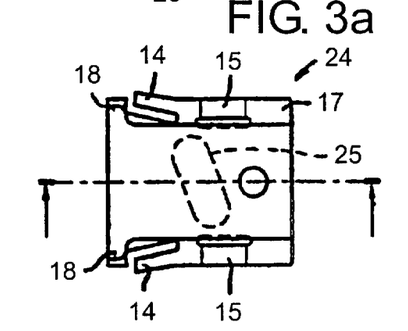
FIGS. 3a–3b show a protective member in a plane view from above and a longitudinal section, respectively.
Figures 3B, 4, 5:
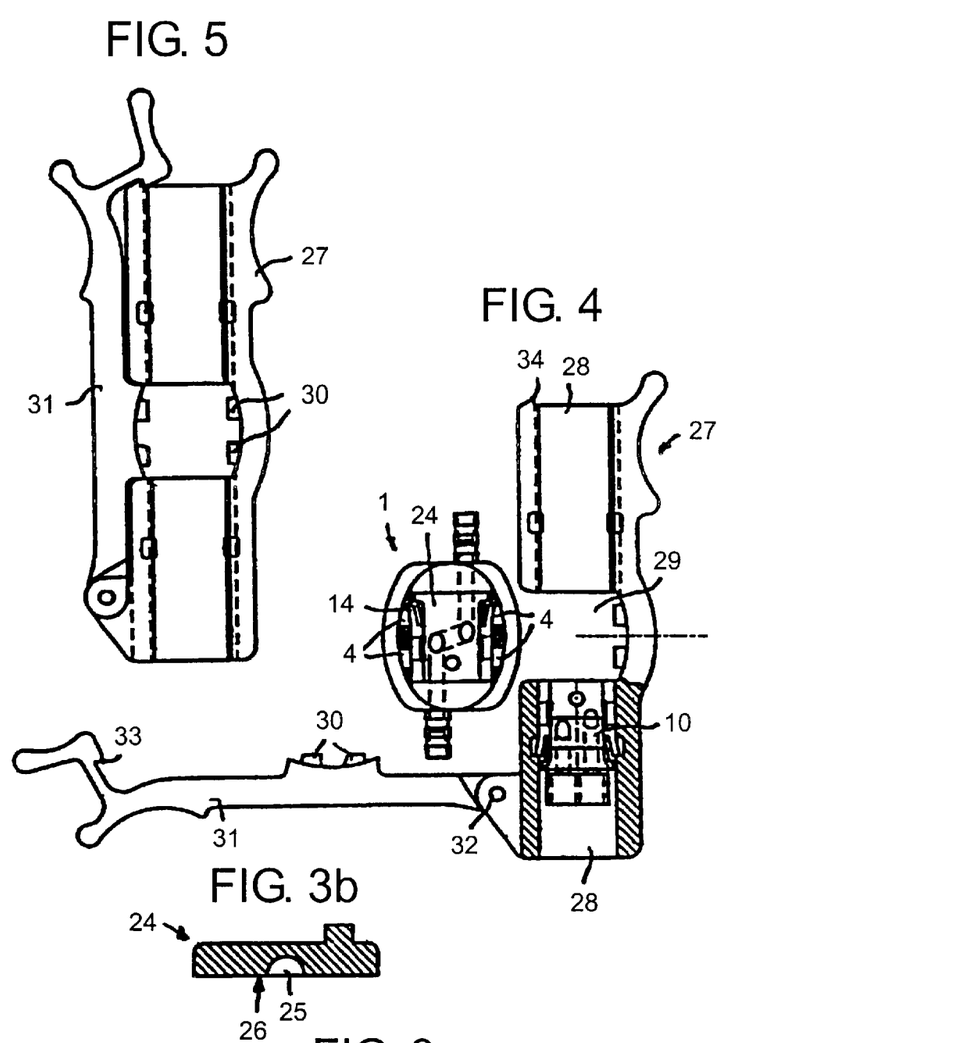
FIG. 4 shows a main body and a protective body with applied connecting member before an imagined connecting process with the protective body having an open holding means.
FIG. 5 shows the protective body having a closed holding means.

The corresponding is also true for other parts intended to be connected to the main body, for example the protective member (see FIGS. 3a–b).

The holding means 17 provides in this case essentially centrally located pressing portions 15 which are comprised of somewhat vaulted resilient portions of the strips 17,. said pressing portions 15 being separated sideways from the main part of the connecting member 10 through slots 16. In use these portions 15 will guarantee safe pressing of the sealing surfaces against each other while allowing adequate absorption of possible play at the holding elements of the main body.

Figure 2B:
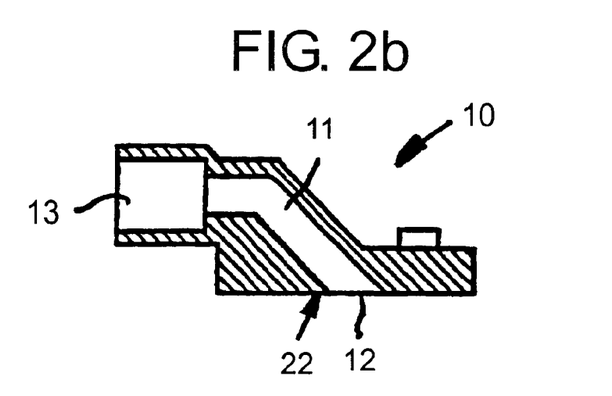

From FIG. 2b the drawing of one of the conduits 11 inside the connecting member, from the second opening 12 with surrounding second sealing surfaces to the nipple portion 13, is more clearly shown.

Figure 2C:
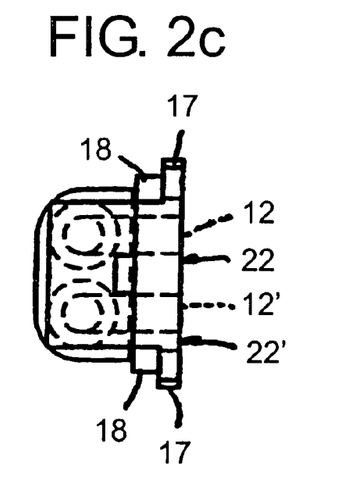

From FIG. 2c the construction of the holding means 17 is shown in more detail and being designed as strip-like guide flanges, and the locking shoulders 18 which through their co-operation with the recesses 19 assure fastening and correspondence with respect to the arrangement of openings. Interrupted lines indicate the second openings 12, 12', and 22, 22' indicate the respective second sealing surfaces.

FIG. 3a shows a protective member 24 with means 14, 15, 17 corresponding to the connecting member. It is further shown that the protective member is essentially plate-like having a transverse oblong recess 25, which in the applied position comprises connection channel between the openings 8, 8' in the main body in order to guarantee a continues flow through the main body. 26 indicates the sealing surface surrounding the recess 25 (best shown in FIG. 3b) and which is co-operating with corresponding sealing surfaces on the main body.

FIG. 4 shows a protective body 27, which also function as a guiding body in respect of the connecting/disconnecting procedures, whereby 28 indicates a linear guide which corresponds to and is intended to coincide with the guide 7 of a main body 1 being inserted into a recess 29 which is adapted for that purpose and which thus is intended to receive the main body 1 surrounding its upper structure 20 (see FIG. 1a), whereby the material thickness of the protective body in the area of the guide is adapted to correspond to the distance between the base plane 21 of the main body 1 and the surface including the sealing surfaces 9, 9'. The protective body guiding body 27 also includes a fastening arm 31, which is pivoted onto the main part of the body at 32 and which is provided with a snap lock means 33 for co-operation with a snap protrusion 34 at the upper part of the main part. Sideways directed projections 30 are adapted, in the inserted position of the main body 1 and the upwards pivoted position of the fastening arm 31, to penetrate the openings 4 in the main body 1 and thereby on the one hand safely grip the main body, on the other hand press the snap wings 14 belonging to a protective member 24 being applied on the main body inwardly in such a way that they will disengage from the respective opening 4. Hereby protective member 24 is thus made free from the main body 1 and may be removed. This is accomplished by the connecting member 10, which is placed in the guide 28 of the protective body 27 being brought in the direction upwards as seen in the figure, whereby thus, at the same time the protective member 24 will come out from the main body 1 and be brought upwardly into the upper part of the guide 28. A continued insertion of the connecting member will result in the shoulders 18 abutting the shoulder recesses 19 while simultaneously the snap wings 14 will come in level with the openings which are most at the bottom of the figure. Final snapping-in will be obtained at the opening of the arm 31, when the projections 30 are removed from the openings 4 whereby safe and adequate locking of the connecting member 10 into the main body 1 is guaranteed. The protective body may now be removed from the main body by the arm 31 being pivoted downwardly and the protective body being brought sideways away from the main body. Through the invention is thus obtained very simple and fast switching from—as an example in case of an implanted blood vessel valve having two couplings—a position with active by-pass function through the channel of the protective member to a position with connected connecting member. In order to assure gathering of the connecting member and the protective member in the displacement direction, and thereby avoid separation in a longitudinal direction of these parts in connection with switching and at the same time simplify the displacement process, a displacement slide is preferably arranged so as to be adapted displaceably on the guide of the protective body and comprising on the one hand means for controlling the position of the elements in the displacement direction, on the other hand for common displacement effect in the form of a "thumb grip" or the like. This arrangement guarantees limited strain to the integration of the skin with the main body.

In order to connect an external circuit, a patient having an implanted main body thus needs a connecting unit including a connecting member applied on and being protected by a protective body for the connecting procedure, and after completed treatment he will need a protective unit consisting of a new protective member applied to and being protected by a new protective body. Both these units are advantageously single use articles.

From FIG. 5 the design of the protective body is shown—the guiding body 27 having upwardly pivoted and snapped-on fastening arm 31. Freeing of the coupling member and by the way of the membrane member from the main body is accomplished in correspondence with what has been said above with respect to the protective member. When a member, coupling member, protective member or membrane member, is to be applied on the main body, the movement of insertion is opposite to the movement of the member to be replaced in the shown embodiment. It is however not excluded that the same movement of insertion be used. In that case the holding arrangement onto the main body is modified.

Figure 6A:
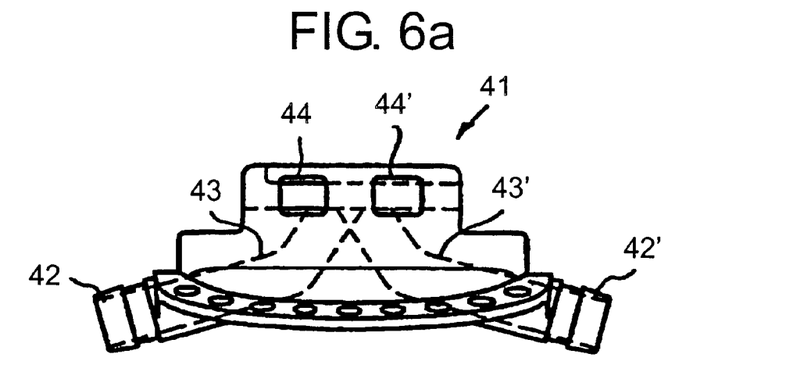
FIGS. 6a–6c show a modified main body in a side view, an end view and a plane view from above, respectively.
Figure 6B:
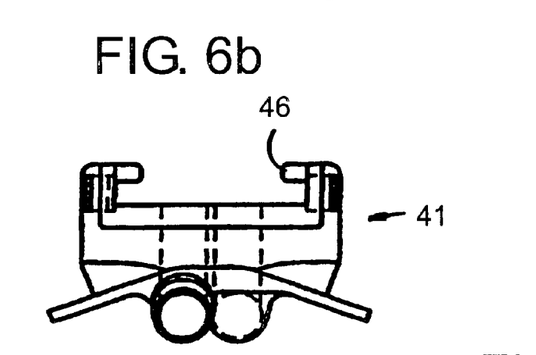
Figure 6C:
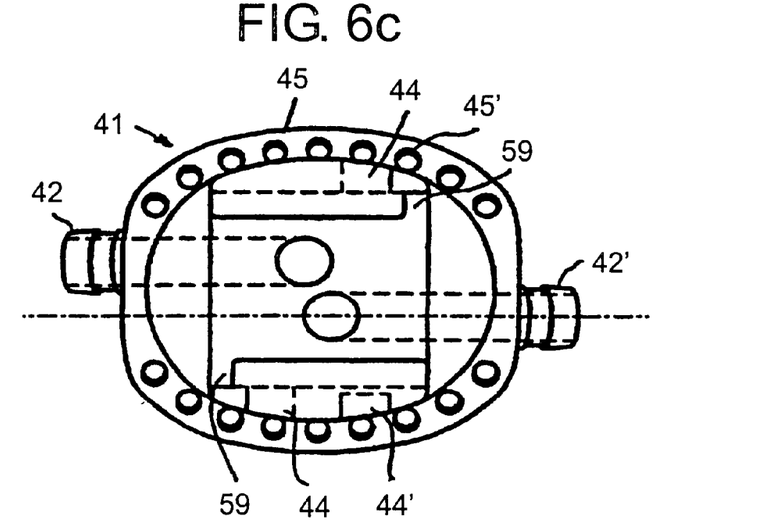

On the modified main body 41 in FIGS. 6a–c the outward coupling means 42 and 42' are directed somewhat obliquely downwards in order to enhance the flow through channels and facilitate placement at implantation. In this case there are only two diagonally located coupling openings 44 in order to assure safety against wrongful connection. 44' concerns a guide opening shaped as an outwardly open one-way hole for co-operation with a sideways directed holder projection in the corresponding protective body/ guiding body. 59 concerns in this case only two diagonally located shoulder recesses. Also these arrangements have the purpose of assuring adequate connection of the different details.

Figure 7A:
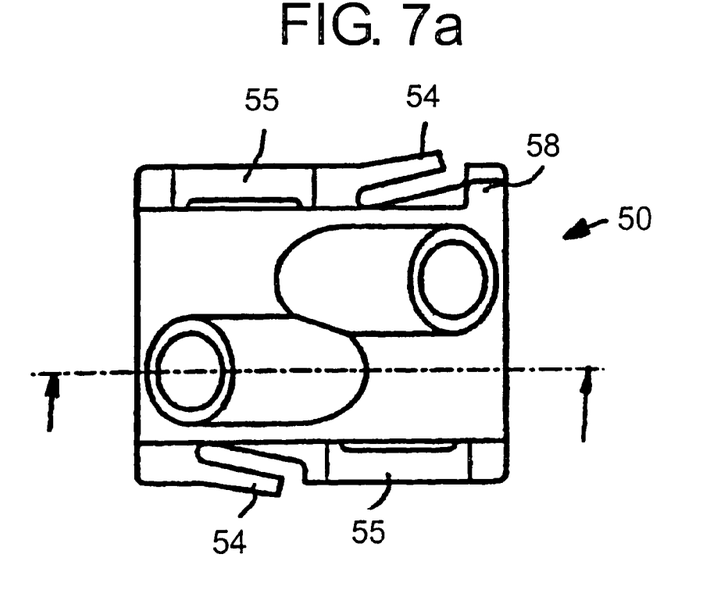
FIGS. 7a–7b show a modified connecting member in a plane view from above and in a longitudinal section.
Figure 7B:
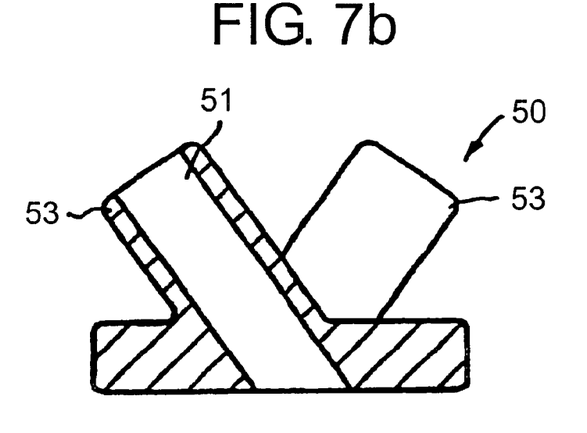

The somewhat modified connecting member 50 in FIG. 7a and b is provided with differently located nipple portions 53, which in this case with their channels 51 are comprised of generally straight continuations of channels 43 and 43' in the main body (see FIG. 6a) which gives reduced flow resistance in the device and thereby enhanced performance and also reduced tendency of forming thrombus. Further, in the connecting member, there is only one locking shoulder 58 and the snap wings 54 and the pressing portions 55 are located diagonally. Altogether this results in eliminating wrongful placement of the coupling member onto the main body.

A further advantage with channel disposition according to the invention is that it allows access to the channels in the main body and to the bloodstream for "thrombectomy", i.e. removing of coagulated blood or the like without surgery.

The invention may be modified within the scope of the following claims and is not limited to the shown embodiments. The invention may thus be used in a device with only one coupling and then as an implant as well as a hose coupling for use outside the human body.

Also other and differently shaped components may be arranged to be connected to the main body, for example a membrane unit which may have a construction essentially as the protective member 24 but having a penetrable membrane limiting the channel 25 from the surroundings. The membrane may in a per se known manner be penetrated with a needle in order to allow blood sampling or introduction of medicals etc. into the blood stream.

Figure 8A:
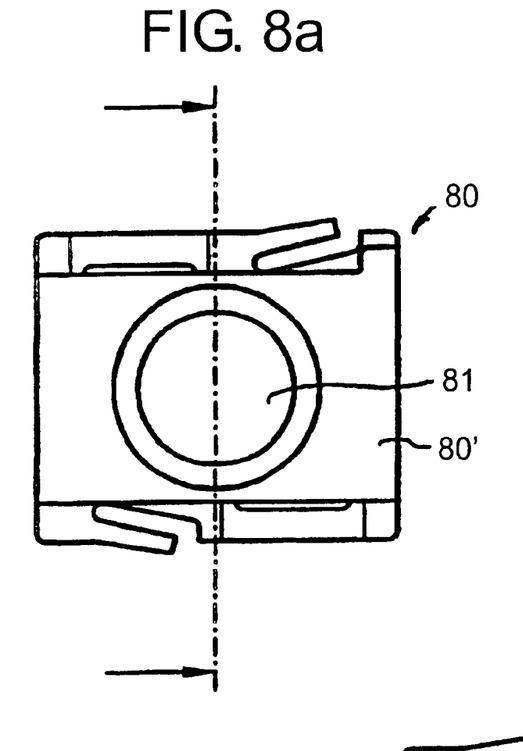
FIGS. 8a–8c show a membrane unit in a plane view from above, from below and in a transverse section, respectively.
Figure 8B:
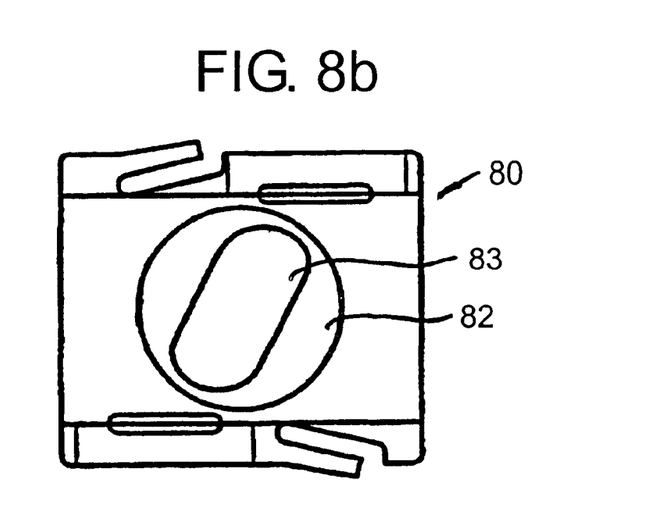
Figure 8C:
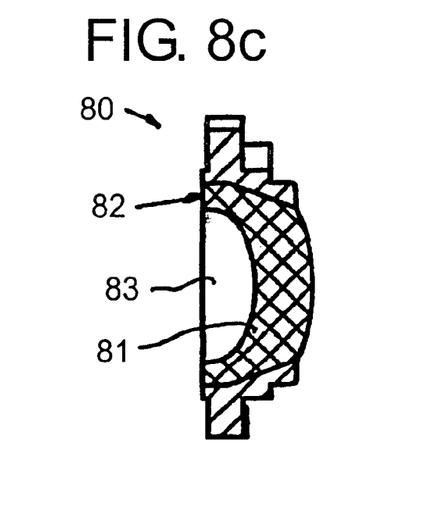

The membrane unit 80 in FIGS. 8a–c thus includes a main part 80' having a body 80' with a through hole into which a penetratable membrane 81 is inserted sealingly. As the case with the protective member in FIGS. 3a–b having the recess 25, here a connection channel 81 is provided which in this case is formed of the material of the membrane, whereby a sealing surface 82 is arranged surrounding the channel 81. This arrangement results in that safe sealing effect may be obtained between this surface 82 and the corresponding surface of the main body, eliminating the need of surface treatment of the surfaces. A membrane unit of this kind may also be allowed to remain, at least during certain periods, on an implanted main body and thus replace particular protective members (FIGS. 3a–b) so that there will be no need of switching between such parts before and after for example blood sampling or drug administration.

As an alternative separate membrane units may be connected to a connecting member over a hose (hoses).

Figure 9:
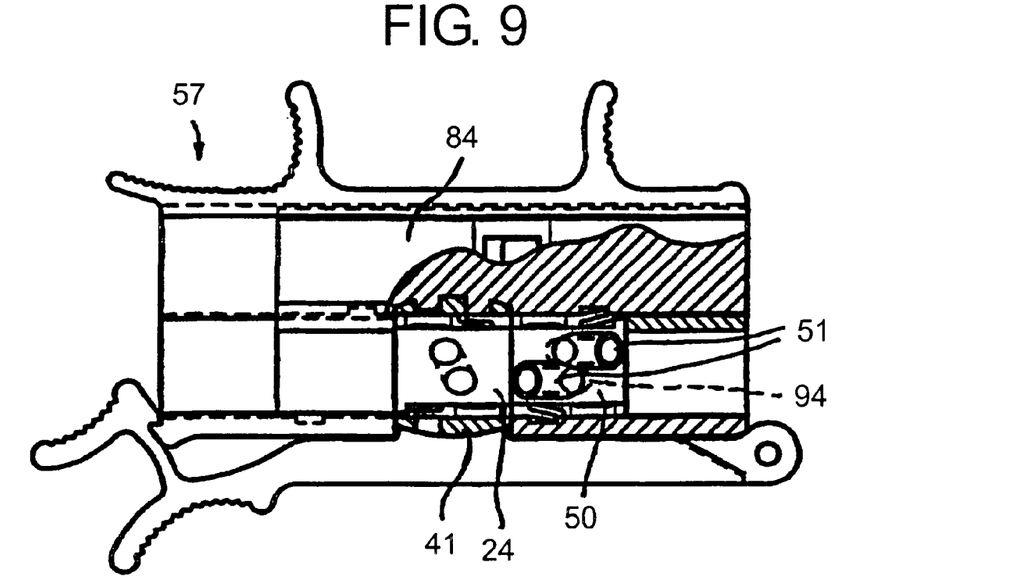
FIG. 9 shows the modified main body of FIG. 6 and a modified protective body having applied connecting member before an imagined connecting process.

FIG. 9 shows an assembly of the modified parts showing the protective body 57 with a displacement slide 84 mounted on a main body 41 and protective member and connecting member 50. 94 indicates a recess in the protective body forming a channel for connection between the conduits 51 of the connecting member. This construction allows prefilling of the channels in question with a liquid such as a salt solution before application of the connecting member in order to avoid introduction of air into the bloodstream resulting in further increased safety against thrombus.

Figure 10A:
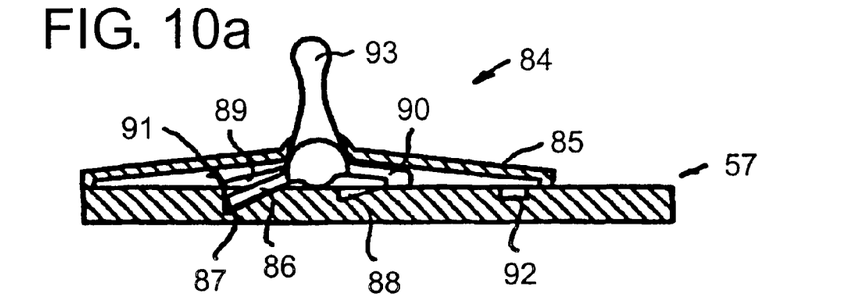
FIGS. 10a and 10b show the protective body of FIG. 9 with the slide in the different displacement positions.
Figure 10B:
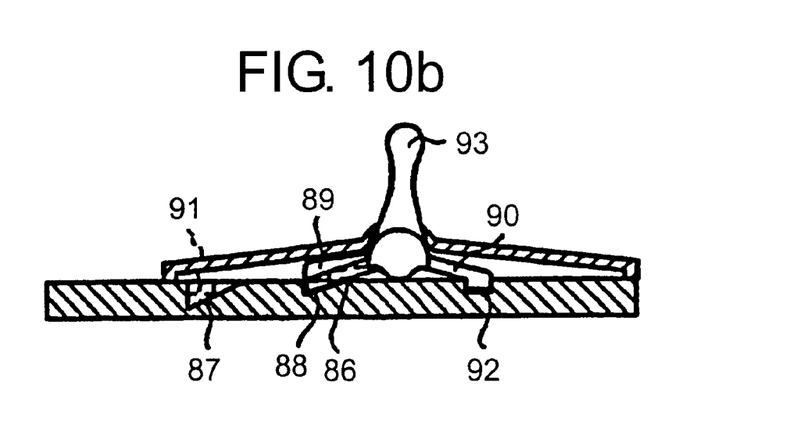

FIG. 10 a shows diagrammatically a protective body 57 with the displacement slide 84 in an initial position, for example with applied connecting member (not shown) to be applied to a main body. The cover portion 85 is covering and prevents manipulation with stopping and locking elements, namely a locking tongue 86 which is placed in a first locking recess 87 in the protective body and first 89 and second 90 pawls, whereof the first in this position co-operates with a first catch recess 91. When connecting for example a connecting member, the hand grip 93 is brought to the right in the figure, whereby the first pawl is freed from its catch recess 91, whereafter the entire slide may be brought to the right. In the right position, in FIG. 10b, the locking tongue 86 co-operates with a second locking recess 38, which is designed as a lock catch for preventing movement to the left in the figure, and the second pawl 90 co-operates with the second catch recess 92. This way the protective body may not be reused unauthorized whereby risks of infections by using potentially infected material is avoided. Protective bodies constructed correspondingly may be used for applying all the additional parts.

The construction of details may deviate from shown embodiments. The guide may thus be arranged differently, for example with means corresponding to the holder elements 6 instead of being placed on connecting member and vice versa. The guide may be curved, the example circular, and the sealing surfaces may be provided on a curved surface as seen perpendicular to the connection direction. The drawing of channels may be arranged differently with the example channels drawn in the same direction instead of in opposite directions.

The placement of and provision of snap means such as snap wings, locking shoulders etc. may deviate from what is shown. Also the elements for freeing a snap-locked connecting member or protective member may be varied with respect to construction and location.

The device may be used as an implant or as a separate coupling device having one or two outgoing couplings as well as openings and conduits in the respective portion. The invention provides several advantages whereof here only will be mentioned that the construction provides a safe, painless and convenient access to the bloodstream, so that it may be advantageously used by the patient in the home instead of by trained personnel at a hospital. This is also the result of using the spontaneous flow as the propellant, i.e. the use of the heart as a pump for propelling the blood through the blood treatment equipment or the like is possible and facilitated by equipment according to the invention.

Materials which may be used are biocompatible if it is needed for the application in question. The construction according to the invention makes manufacture in synthetic materials well adapted, possibly having surfaces treating with blood or/and biocompatible coatings for all the parts in question. The parts may then be comprised of single use articles which are possible to produce at a low cost. Also manufacture in other material such as titanium or titanium alloys, possibly having surfaces provided with blood and/or biocompatible layers for the implantable main body, may come into question.

What is claimed is:

1. Device for external connection of the bloodstream of a patient to an external circuit or a fluidum source for medical purposes, said device comprising:
    a main body with at least a first opening surrounded by a first sealing surface and communicating with an outward coupling means for connection to the bloodstream, wherein in a non-connected position, the first sealing surface being adapted to be protected by a removable protective member, and
    a connecting member with at least one second opening surrounded by a second sealing surface and for communicating with said external circuit or fluidum source, which in a non-connected position is arranged to be protected by a protective body which is removable with respect to the connecting member,
    the connecting member being connectable to the main body under simultaneous removal of the protective member from the first sealing surface and the protective body from the second sealing surface in order to obtain co-operation between the first and second sealing surfaces and obtaining a leakproof connection between said openings,
    the main body being provided with holding elements for the co-operation with holding means on the protective body and the connecting member, respectively, said holding elements forming a guide open at two ends for the protective member and the connecting member, respectively.

2. Device according to claim 1, wherein the guide is linear.

3. Device according to claim 1, wherein the guide is curved.

4. Device according to claim 1, wherein the sealing surfaces are planar.

5. Device according to claim 1, wherein the main body is implantable and is provided with flange-like means having several through holes for supporting growth of human tissue.

6. Device according to claim 1, wherein there are two of said coupling means and two of said first and two of said second openings.

7. Device according to claim 1, wherein one of the main body on the one hand and the connecting member and the protective member on the other hand is provided with snap lock means for mutual fastening in a respective applied position.

8. Device according to claim 6, wherein the protective member is provided with a channel for interconnecting the two first openings in an applied position.

9. Device according to claim 1, wherein the protective body is provided with means for co-operation with the main body so that the connecting member before application thereon is directed into said guide.

10. Device according to claim 9, wherein said means are comprised of lockable and openable fastening means.

11. Device according to claim 1, further comprising a conduit member including a penetratable membrane, which allows access to the opening of the main body, where a resilient sealing surface is arranged.

12. Device according to claim 1, wherein holding means provides integral resilient pressing portions.

13. Connecting unit for use with a device for external connection of the bloodstream of a patient to an external circuit or a fluidum source for medical purposes, the connecting unit comprising a connecting member with at least one opening surrounded by a sealing surface, for communicating with an external circuit or a fluidum source, and in a non-connected position being arranged to be protected by a protective body which is removable in respect of the connecting member, whereby the connecting member is provided with holding means which are adapted to co-operate with holding elements on a main body, which form a guide which is open at two ends, and whereby the protective body carries means for co-operation with the main body such that the connecting member before application thereto is arranged to be directed onto said guide.

14. Connecting unit according to claim 13, wherein said means are comprised of lockable and openable fastening means, respectively.

15. Connecting unit according to claim 13, wherein the protective body is provided with a displacement slide, which together with the protective body comprises locking means for preventing replacement after completed connecting displacement.

16. Protective unit for use with a device for external connection of the bloodstream of a patient to an external circuit or a fluidum source for medical purposes, said protective unit comprising a protective member with protective surfaces and a protective body which is removable in respect of the protective member, whereby the protective member is provided with holding means which are adapted to co-operate with holding elements on a main body, which form a guide which is open at two ends, and whereby the protective body carries means for co-operation with the main body such that the protective member before application thereto is arranged to be directed onto said guide.

17. Protective unit according to claim 16, wherein means are comprised of lockable and openable fastening means respectively.

18. Protective unit according to claim 16, wherein the protective body is provided with a displacement slide, which together with the protective body comprises locking means for preventing replacement after completed connecting displacement.

* * * * *